Figure 1:
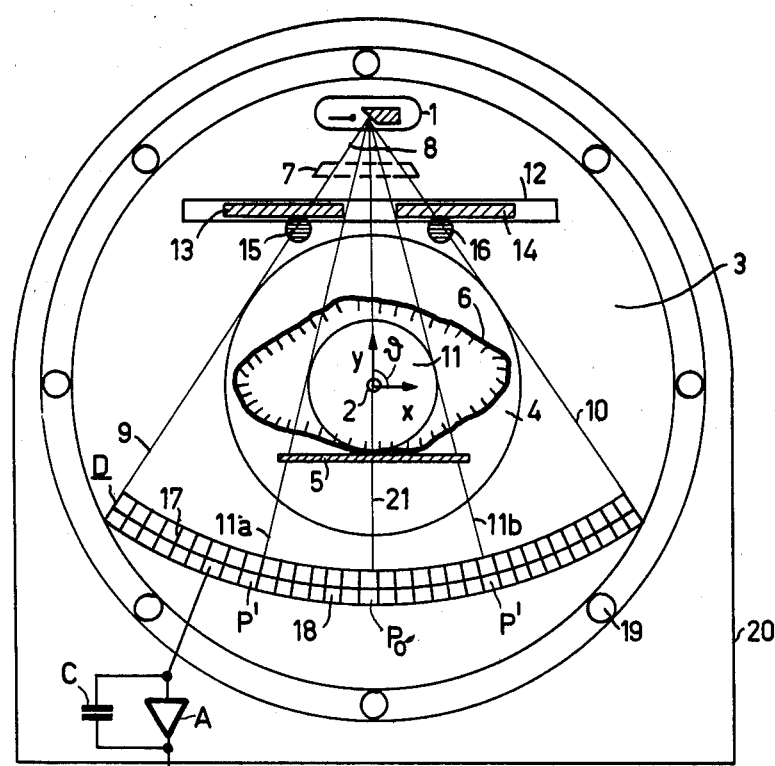

United States Patent [19]

Wagner

[11] 4,394,738
[45] Jul. 19, 1983

[54] METHOD OF AND DEVICE FOR DETERMINING THE DISTRIBUTION OF RADIATION ABSORPTION IN A SLICE OF A BODY

[75] Inventor: Wolfgang Wagner, Hamburg, Fed. Rep. of Germany

[73] Assignee: U.S. Philips Corporation, New York, N.Y.

[21] Appl. No.: 216,478

[22] Filed: Dec. 15, 1980

[30] Foreign Application Priority Data

Jun. 16, 1979 [DE] Fed. Rep. of Germany ....... 2924423

[51] Int. Cl.³ .......................... A61B 6/00; G01N 23/00
[52] U.S. Cl. .......................................... 364/414; 378/4
[58] Field of Search .................... 364/414; 250/445 T, 250/523, 361 R, 363 S; 358/166, 110

[56] References Cited

U.S. PATENT DOCUMENTS

| | | | |
|---|---|---|---|
| 4,257,102 | 3/1981 | Horiba et al. ........................ | 364/414 |
| 4,309,614 | 1/1982 | Wagner ........................... | 250/445 T |
| 4,323,977 | 4/1982 | Arseneau ............................. | 364/571 |
| 4,324,978 | 4/1982 | Kalender et al. ................ | 250/445 T |
| 4,333,145 | 6/1982 | Heuscher et al. ................... | 364/414 |

*Primary Examiner*—Edward J. Wise
*Attorney, Agent, or Firm*—Jack E. Haken

[57] ABSTRACT

If only the absorption distribution of a part, for example, a separate organ, of a body slice to be examined is desirable, the radiation dose administered to the body can be limited. The part is irradiated with the full intensity only during a first measuring cycle. In order to avoid reconstruction errors, the entire body slice is irradiated with a second intensity during a second measuring cycle which is substantially lower than the first intensity. Thus, along each measuring path through the part of the slice there are available two absorption values wherefrom suitable correction factors can be determined for correction of all second absorption values which subsequently no longer exhibit any deviations, or only small deviations, with respect to the first absorption values, so that they do not introduce artefacts during the reconstruction.

7 Claims, 8 Drawing Figures

METHOD OF AND DEVICE FOR DETERMINING THE DISTRIBUTION OF RADIATION ABSORPTION IN A SLICE OF A BODY

The invention relates to a method of determining the distribution of radiation absorption in a flat examination zone in a body which is situated within a positioning zone which completely encloses the examination zone, the examination zone being completely irradiated in different measuring directions which are situated within the examination zone along a large number of measuring paths by means of radiation of a first intensity in order to determine first measurement values, the part of the positioning zone which is situated outside the examination zone being irradiated in a corresponding number of measuring directions along measuring paths by means of radiation of a second intensity which is lower than the first intensity in order to determine second measurement values, first absorption values being determined from the first measurement values and second absorption values being determined from the second measurement values, said absorption values being used for the reconstruction of the distribution of the radiation absorption.

A method and a device of this kind are already known from Canadian Pat. No. 1,072,688. Therein, a fan-shaped radiation beam emitted by a radiation source is stopped down by means of a diaphragm device so that the radiation beam irradiates only the examination zone, corresponding to a zone in the body slice to be reconstructed, with an unattenuated intensity for the determination of the absorption values. The radiation of the radiation beam which extends outside the examination zone is strongly but not completely absorbed by the diaphragm device, so that outside the zone the body slice is irradiated with a substantially lower intensity. Because the measurement values of the radiation extending outside the examination zone contain a comparatively large amount of noise, radiation absorption coefficients can be derived therefrom only with a limited accuracy.

A method of this kind for the determination of the absorption distribution is suitable for significantly reducing the radiation dose whereto a body is exposed, for example, if a given part of the body, for example, a separate organ of a human body, which is situated within the body slice has to be examined. In order to avoid large reconstruction errors in the examination zone if the section of the body is larger than the examination zone, it is necessary to determine not only measurement values associated with measuring paths through the examination zone, but also measurement values associated with measuring paths extending outside the examination zone (see W. Wagner, "Reconstruction from truncated scan data", published in Mediata, special issue 1/78).

However, due to the presence of the diaphragm device, the radiation extending outside the examination zone according then has a mean radiation energy which is higher than the radiation extending through the examination zone ("radiation hardening"). The corrections of the absorption values which are necessary in view of the different mean radiation energies in order to obtain a correct reconstruction of the absorption distribution, however, necessitate complex arithmetical operations, so a comparatively long calculation time.

Moreover, according to a described method a part of the scattered radiation produced in the examination zone is measured by detectors which are intended to measure the radiation of reduced intensity which extends outside the examination zone; this causes inaccurate second measurement values.

The invention has for its object to provide a method of and a device for determining the distribution of radiation absorption in a slice of a body where the amount of radiation whereto the body is exposed is substantially reduced, without difficult corrections of the measurement values due to different mean radiation energies and without scattered radiation corrections being required.

A method in accordance with the invention is characterized in that during a first measuring cycle the examination zone of the body slice to be examined is irradiated with the first intensity in order to determine the first measurement values, whilst during a second measuring cycle the total positioning zone of the same or a neighbouring body slice is irradiated with the second intensity in order to determine second measurement values.

Herein, a measuring cycle is to be understood to mean the irradiation of a body slice in all measuring directions situated in the slice by means of a number of measuring beams for the recording of the first or second measurement values required for the reconstruction of a distribution of the radiation absorption. Such a radiation beam may be fan-shaped. The measurement values obtained may be selected to form groups of measurement values so that the measuring paths associated with a group of measurement values extend in parallel. The term first and second measuring cycles does not imply any sequence in time whatsoever. The second measuring cycle may directly follow the first cycle, but may also have been performed at an earlier instant. Simultaneous execution of the two measuring cycles, however, does not take place.

Tests have revealed that for the determination of the absorption distribution in the examination zone it suffices that the second measurement values along measuring paths extending outside the examination zone are at least approximately known. This means that less severe requirements may be imposed as regards the absence of noise and the accuracy of the second measurement values than on the measurement values determined along measuring paths extending through the examination zone, so that the determination of second measurement values outside the examination zone may be performed with a substantially lower radiation intensity. The second measurement values may also be measured in a slice adjoining the body slice.

When the mean radiation energies of the radiation during the first and the second measuring cycle are at least approximately equal, first and second absorption values which correspond to the integral of the radiation absorption in the body along the relevant measuring paths can be determined from the measurement values obtained, so that the absorption values need not be corrected for the different mean radiation energies.

In a further embodiment in accordance with the invention, the body is displaced in a direction transversely of all measuring directions in order to irradiate at least one second body slice which adjoins a first already irradiated body slice, after which only an examination zone in the second body slice to be examined is irradiated with radiation of the first intensity in order to determine first absorption values, the second absorption values of the first irradiated body slice whose associated measuring paths extend outside the examination zone being used for each measuring direction as approximated second absorption values for the reconstruction of the radiation absorption distribution in the second body slice.

This is because it is often necessary to determine the internal structure of a body in a three-dimensional zone. This is usually achieved by the reconstruction of the absorption distribution in different, adjoining parallel body slices. If the examination zones in the various body slices are at least approximately equally large and occupy approximately the same position in the examination plane, it is merely necessary to irradiate only one body slice, for example, the first body slice, in order to record first and second measurement values. For all other body slices, only the examination zone is irradiated with radiation of a first intensity in order to determine first measurement values or first absorption values; this results in an important reduction of the radiation dose whereto the body is exposed or in a substantial reduction of the time required for determining a sufficient number of measurement values for the reconstruction of the absorption distribution of the irradiated body slices.

In a further preferred embodiment in accordance with the invention, the second intensity which is lower than the first intensity is adjusted by reduction of the tube current of an X-ray source, so that the radiation energy spectrum of the X-ray tube remains the same, with the result that no correction of the absorption values due to different mean radiation energies in the successive first and second measuring cycles is necessary.

Between the first and the second absorption values disturbing deviations often occur inter alia due to: movement of the patient, drift in the radiation spectrum of the radiation source and, in the case of irradiation of several adjacent body slices, also due to structures in the body. Therefore, the second measurement values are also determined along measuring paths through the examination zone. From the first and the second measurement values first and second absorption values, respectively, are then determined in the manner to be described hereinafter.

According to a further version of the method in accordance with the invention, for each measuring direction there is formed a correction factor whereby the second absorption values whose associated measuring paths extend outside the examination zone are multiplied in order to form approximated second absorption values, the correction factor being determined by dividing all first absorption values which are associated with one measuring direction and with measuring paths extending through the examination zone by the second absorption value associated with the same measuring path, after which all quotients are arithmetically averaged in order to determine the correction factor.

A measuring path extending through the examination zone has associated with it two absorption values whereby a suitable correction factor is determined for reducing the said deviations so that the second absorption value along a measuring path through the examination zone exhibits no deviations or only small deviations with respect to the first absorption values along the same measuring path. A correction factor is then calculated for each measuring direction.

Tests have demonstrated that the correction factors which lead to a high degree of correspondence between the first and the second absorption values within the examination zone can be used for determining approximated second absorption values whose associated measuring paths extend outside the examination zone. The second absorption values determined outside the examination zone are then multiplied by an associated correction factor.

A preferred version of a method in accordance with the invention is characterized in that during the first and the second measuring cycle a source for generating the penetrating radiation is situated at a first and a second distance, respectively, from the examination zone, the first distance being smaller than the second distance.

Embodiments in accordance with the invention will be described in detail hereinafter with reference to the accompanying diagrammatic drawing.

Figure 4:
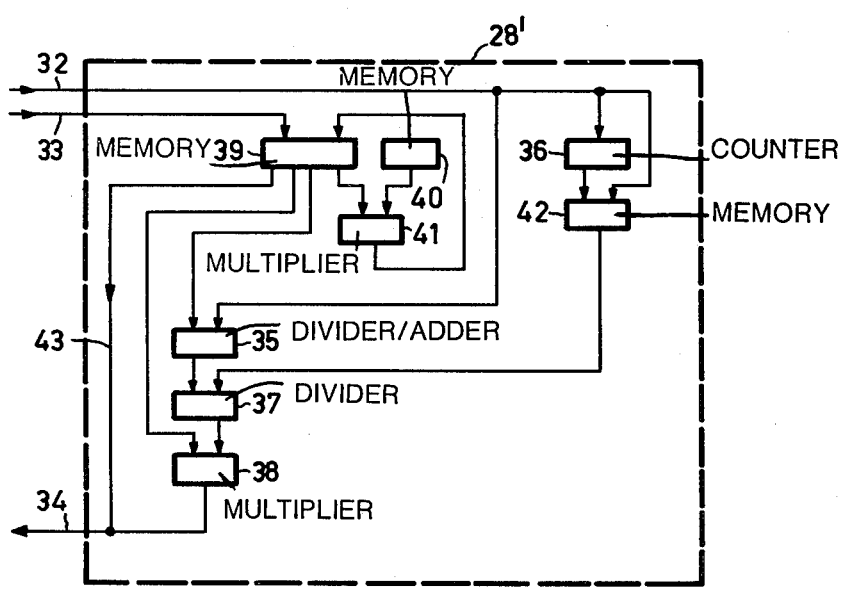
Figure 3:
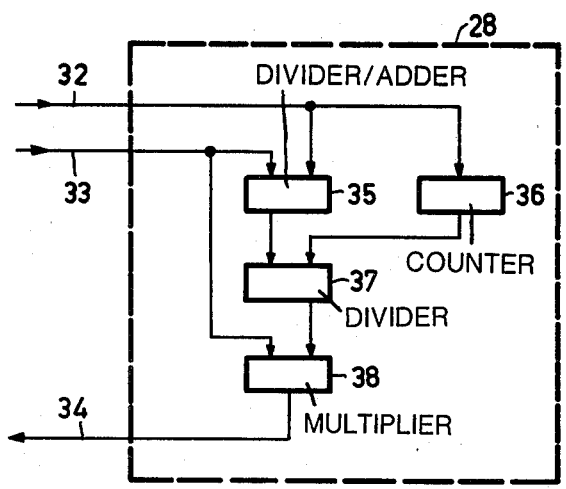
Figure 4:
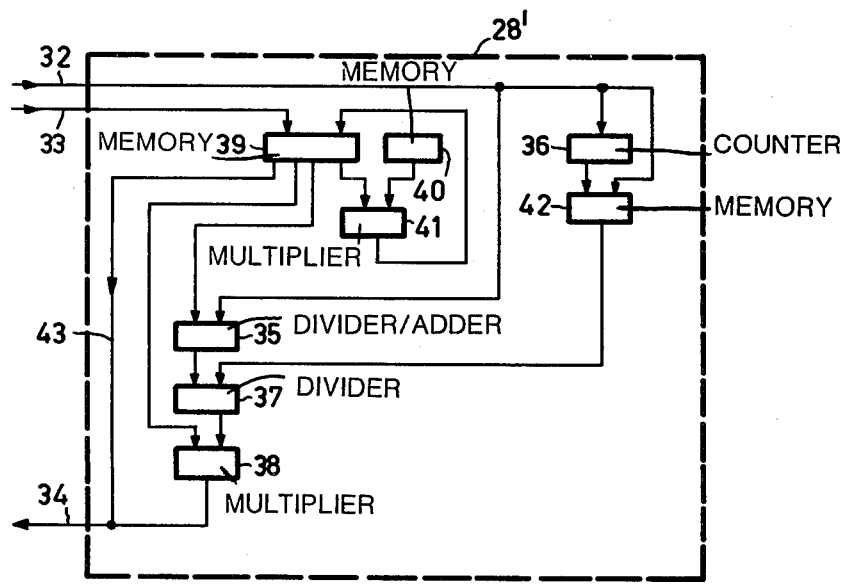
Figure 5:
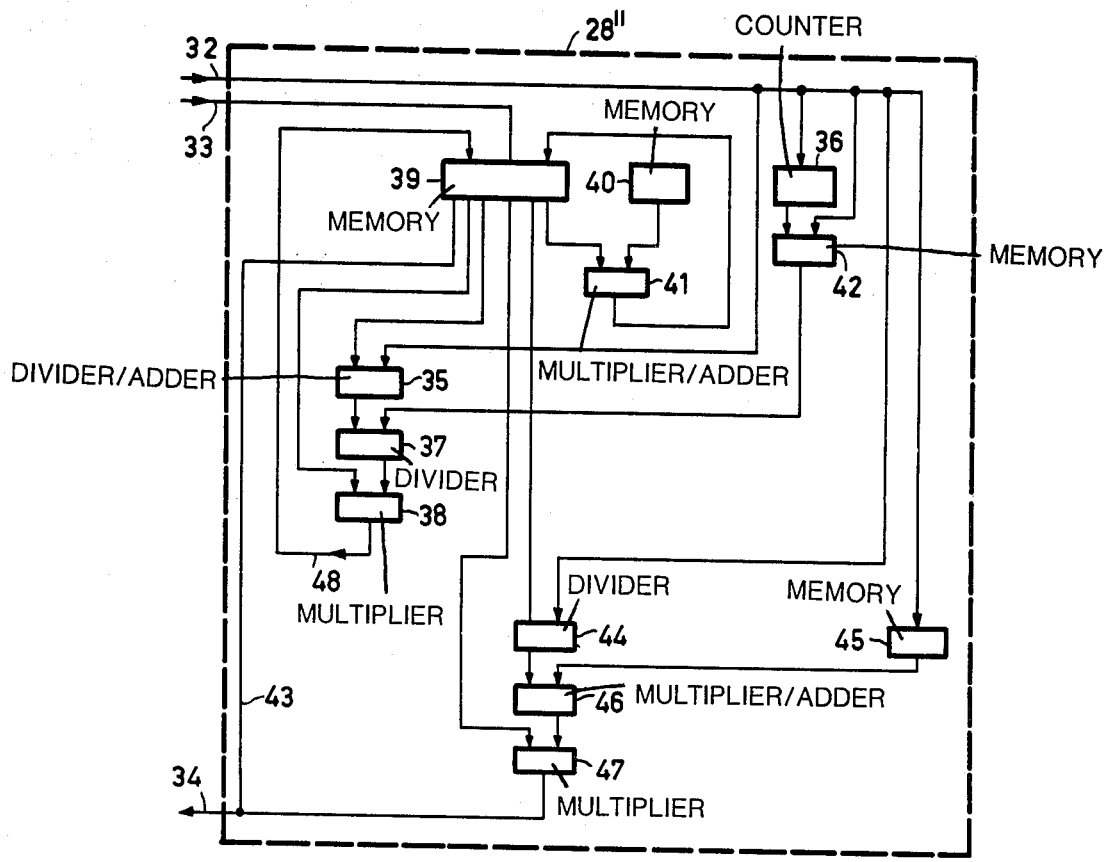
Figure 6A:
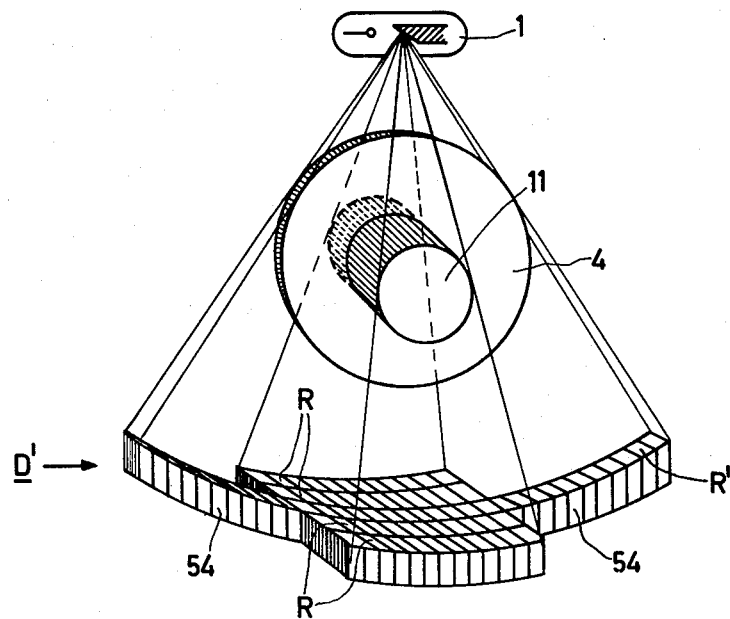

FIG. 1 shows an X-ray tomography apparatus for measuring first and second measurement values, comprising a displaceable diaphragm device, FIG. 1a shows a preferred embodiment of an X-ray tomography apparatus for measuring first and second measurement values, FIGS. 2, 3, 4 and 5 show different block diagrams for the processing of the measurement values determined in accordance with the invention, and FIGS. 6a, b show embodiments of detector devices comprising more than one row of detectors.

FIG. 1 diagrammatically shows a tomography apparatus which comprises a radiation source 1, for example, an X-ray tube, which is arranged on a support 3 which is rotatable about a system axis 2 which extends perpendicularly to the plane of the drawing. The support 3 may be, for example, a flat plate which comprises an opening which is concentric with the system axis 2 and which determines the size and the position of a positioning zone 4 for a body 6 arranged on a patient table 5. The radiation emitted by the radiation source 1 is stopped down by means of a first diaphragm 7 so that a fan-shaped, flat radiation beam 8 is obtained whose extreme rays 9 and 10 are tangent to the positioning zone 4. In order to reduce the angle of aperture of the radiation beam 8 or for stopping down the radiation beam 8 to an examination zone 11 which is preferably concentric with the system axis 2 there is provided a further diaphragm device 12 which comprises absorption pieces 13, 14 which completely absorb the radiation of the radiation beam 8 and which are arranged to be displaceable by means of drive disks 15, 16. The intensity of the radiation emitted by the radiation source 1 is measured by means of a row of detectors D which consists of separate radiation detectors 18 which comprise collimators 17. Each radiation detector 18 is formed, for example, by an ionization chamber and is connected to an integrating amplifier A, C. Via a multiplex circuit MUX, whereto further amplifiers of the other detectors 18 are also connected, the integrated measurement signal is periodically sampled and is applied, via an analog-to-digital converter A/D, and a connection 22, to a processing circuit yet to be described. The measuring rays 11a and 11b which are tangent to the examination zone 11 are incident on the radiation detectors 18 whose positions within the row of detectors D are denoted by the reference p'. p' is, for example, the number of the twelfth radiation detector, taken from the radiation detector which occupies the central position $p_o$ and on which the central ray 21 of the radiation beam 8 impinges. Therefore, if the width of all radiation detectors 18 is the same, the number p' is a measure for the distance between the radiation detector associated with a position p and the radiation detector occupying the position $p_o$.

The two diaphragm devices 7 and 12 and the row of detectors D are mounted on the support 3 which itself is rotatably journalled in a frame 20 by means of suitable bearings 19. If the centre of the examination zone 11 is not situated on the system axis 2, the position of the absorption pieces 13, 14 of the diaphragm device 12 is changed so that the central rays 11a, b are tangent to the examination zone 11 in any rotary position of the support 3. The position and the size of the examination zone 11 are then suitably adjusted prior to the irradiation of the body 6 or the body slice. The described adjustment of the diaphragms is known per se from Canadian Pat. No. 1,072,688. Hereinafter it is assumed that the centre of the examination zone 11 coincides with the system axis 2.

For the determination of a radiation absorption distribution in a slice of the body 6, the body is irradiated in two measuring cycles. During one measuring cycle, the support 3 is rotated for example through 360°, whilst the body 6 or the examination zone 11 is successively irradiated in, for example, 600 different measuring directions, denoted by the angle $\theta$ which is enclosed by the central ray 21 of the fan-shaped radiation beam 8 and the x-axis of a rectangular coordinate system $\{x, y\}$ which is situated in the slice. The origin of the coordinate system $\{x, y\}$ is situated on the system axis 2. The separate radiation detectors 18 supply measurement values $I(p,\theta)$ which are dependent on the angle $\theta$ as well as on the position p of a separate radiation detector 18 in the detector row D.

During a first measuring cycle, the absorption pieces 13, 14 stop down the fan-shaped radiation beam 8 so that only the preselected examination zone 11 is irradiated with radiation of a first (primary) intensity $I_{01}$ in order to measure first measurement values $I_1(p,\theta)$. The radiation which would otherwise extend along measuring paths outside the examination zone 11 is, therefore, completely absorbed.

During a second measuring cycle, the absorption pieces 13, 14 are completely moved out of the path of the radiation beam 8, so that the total positioning zone 4 (and hence the total body slice) is irradiated with a second intensity $I_{02}$ which is substantially lower, for example, more than ten times lower, than the first intensity $I_{01}$ in order to measure second measurement values $I_2(p,\theta)$. The intensity variation is realized, for example, by reducing the tube voltage of the X-ray tube or the radiation source 1, so that radiation having a different mean radiation energy is generated. The variation of the intensity of the radiation and the displacement of the absorption pieces 13, 14 can be coupled, so that when an adjustment device is operated (not shown), the variation and the displacement are performed, the absorption pieces 13, 14 restricting the radiation beam 8 to the examination zone 11 for a preselected first intensity $I_{01}$, whilst the absorption pieces 13, 14 are moved out of the path of the radiation beam for the preselected second intensity $I_{02}$, after which the total positioning zone 4 is irradiated.

The restriction of the fan-shaped radiation beam 8 to the examination zone 11 during the first measuring cycle, however, can also be realized in a manner other than by displacement of the absorption pieces 13, 14. For example, in the absence of a diaphragm device 12, the radiation source 1 and the row of detectors D can be shifted in the direction of the central ray 21 so that the extreme rays 9, 10 of the fan-shaped radiation beam 8 bound the examination zone 11 as will be described in detail hereinafter.

FIG. 1a diagrammatically shows a further embodiment of a computer tomography apparatus for determining first and second measurement values during a first and a second measuring cycle. The apparatus shown comprises an X-ray source 1 which emits an X-ray beam 8 having a fixed angle of aperture $\alpha$. The parts of the tomography apparatus which correspond to FIG. 1 are denoted by the same reference numerals or letters. The X-ray source 1 and the detector row D are movably mounted at a fixed distance from each other on a frame 50. The frame 50 is coupled on both sides, via a rack and pinion 51, to two electric motors 52 whereby the frame 50 with the X-ray source 1 and the detector row D can be displaced with respect to the system axis 2. The frame 50 comprises an oval aperture 53 which leaves the positioning zone 4 completely exposed in all positions of the frame 50 with respect to the system axis 2. For the first measuring cycle, the frame 50 is moved to the position shown, so that the X-ray source 1 irradiates only the examination zone 11. The extreme rays 9, 10 of the X-ray beam 8 form the rays 11a, 11b (see FIG. 1) which are tangent to the examination zone 11. After completion of the first measuring cycle, the frame 50 is moved for the second measuring cycle to a position (denoted by broken lines and the reference numeral 50') in which the source 1' irradiates the entire positioning zone 4. The extreme rays 9 and 10 of the X-ray beam 8 are then tangent to the positioning zone 4. The reference numerals of the parts displaced (such as the frame 50) are provided with an accent in the position for the second measuring cycle.

The embodiment of the tomography apparatus shown in FIG. 1a offers a better resolution for the examination zone 11 than the tomography apparatus shown in FIG. 1. This is because the tomography apparatus shown in FIG. 1a utilizes all detectors of the detector row D for detecting radiation along measuring paths through the examination zone 11. In the apparatus shown in FIG. 1, however, only a part of the detectors of the detector row D are used. When use is made of the apparatus shown in FIG. 1a, a reconstructed image of the examination zone 11 can contain as many pixels as a reconstructed image of the total positioning zone 4 made by means of the apparatus shown in FIG. 1.

The spacing of the measuring paths in the examination zone 11 is smaller during the first measuring cycle than the spacing of the measuring paths in the examination zone 11 during the second measuring cycle. For the processing of the measurement values associated with the measuring paths the spacing must be the same as will be described in detail hereinafter. Interpolation between the measurement values obtained during the second measuring cycle produces a new set of (artificial) measurement values which belong to fictitious measuring paths with an adapted spacing (adapted to the spacing of the first measuring cycle).

It is to be noted that the apparatus shown in FIG. 1a is known per se from U.S. Pat. No. 4,134,020.

Figure 2:
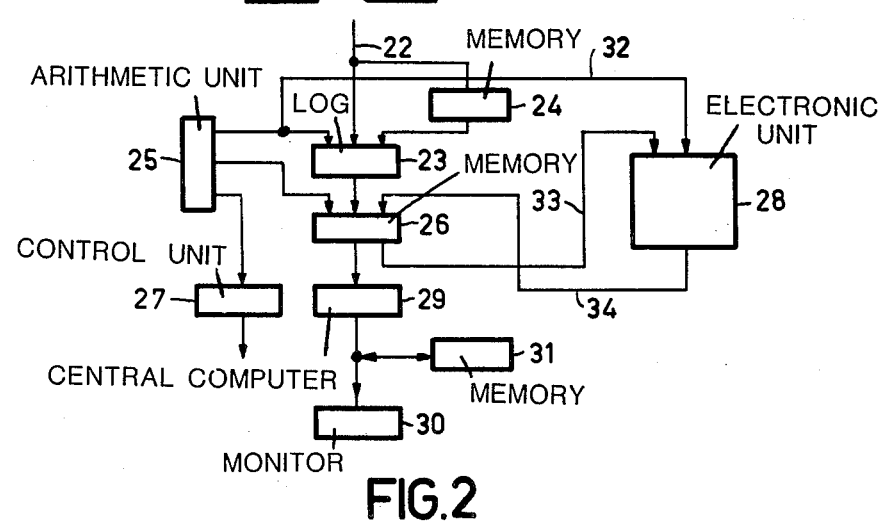

The processing of the first and the second measuring values $I_1(p,\theta)$ and $I_2(p,\theta)$, respectively, will be described with reference to the block diagram shown in FIG. 2. The first and the second measuring values $I_1(p,\theta)$ and $I_2(p,\theta)$, respectively, are applied, via a data line 22, to a first input of a logarithmic conversion device 23 by means of which the first absorption values $Q_1(p,\theta) = -\ln (I_1(p,\theta)/I_{01})$ and the second absorption values $Q_2(p,\theta) = -\ln (I_2(p,\theta)/I_{02})$ are formed. The primary first and second intensities $I_{01}$ and $I_{02}$, being preselected and measured, for example, by calibration measurements by means of the detectors 18, are stored for this purpose in a first memory 24, a second input being connected to the logarithmic conversion device 23. The device 23 comprises, for example, a divider circuit whose output is connected to a read-only memory in which a logarithmic conversion table is stored. On the basis of the position of the centre of the examination zone 11 and the measuring direction $\theta$ the arithmetic unit 25 calculates the coordinates of the extreme rays 11a and 11b which are tangent to the examination zone 11, and hence the positions p' of the two associated detector elements 18. This calculation is predetermined by the geometry of the device and has to be performed only if the examination zone 11 is eccentrically situated with respect to the system axis 2. If the centre of the examination zone coincides with the system axis 2, the positions p' are the same for all measuring directions $\theta$.

The positions p' are applied to a second memory 26 in which the first absorption values $Q_1(p,\theta)$ and the second absorption values $Q_2(p,\theta)$ are separately stored. The positions p' are applied to the device 23 for logarithmic conversion, so that the first absorption values $Q_1(p,\theta)$ associated with measuring paths extending through the examination zone 11 are determined. During the measurement of the first measurement values, a control unit 27 is controlled by the positions p' determined in the arithmetic unit 25 which are dependent on the angle $\theta$ in the case of an accentrically situated examination zone 11. The control unit 27 drives, for example, an electric motor which realizes the displacement of the absorption pieces 13, 14 for the stopping down of the fan-shaped radiation beam 8 during the determination of the first measurement value $I_1(p,\theta)$.

From the first absorption values $Q_1(p,\theta)$ and the second absorption values $Q_2(p,\theta)$ approximated second absorption values $Q'_2(p,\theta)$ are determined by means of an electronic unit 28 (to be described in detail hereinafter) for the measuring paths extending outside the examination zone 11, said approximated second absorption values being used, together with the first absorption values $Q_1(p,\theta)$, to determine the absorption distribution $\mu(x, y)$ of the irradiated body slice by means of a known central computer 29. The absorption distribution $\mu(x, y)$ obtained is stored in a memory 31 and can be displayed, for example, on a monitor 30. The positions p' which indicate the position of the extreme rays 11a and 11b tangent to the examination zone 11 are applied to the unit 28 via the data line 32. Via the data line 33, the first and the second absorption values $Q_1(p,\theta)$ and $Q_2(p,\theta)$, respectively, are applied to the electronic unit 28, whilst via the data line 34 the approximated second absorption values $Q'_2(p,\theta)$ are returned from the electronic unit 28 to the memory 26, the absorption values $Q_2(p,\theta)$ then being replaced by the approximated absorption values $Q'_2(p,\theta)$.

Figure 3:
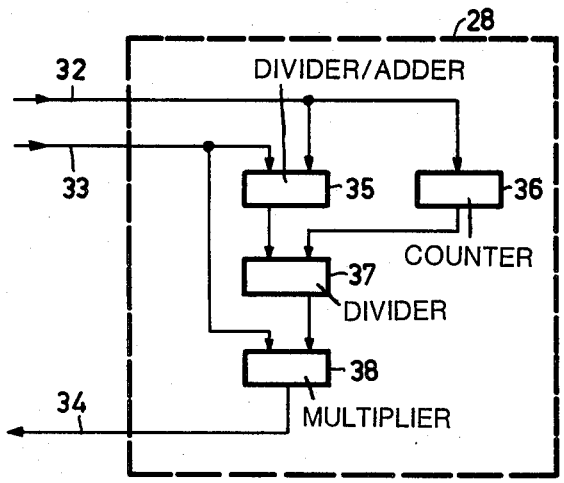

FIG. 3 is a detailed view of the electronic unit 28 for determining the approximated second absorption values $Q'_2(p,\theta)$. It is assumed that a first and a second measuring cycle are performed for a body slice to be examined and that no movements of the body occur. It may then also be assumed that deviations in the first and the second measuring values along one and the same measuring path during the first and the second measuring cycle are caused mainly by different radiation energy spectrums used in the two successive measuring cycles. It is generally applicable that the primary intensity $I_0$ is dependent of the radiation energy E, so $I_0(E)$. Because the radiation absorption is also dependent on the energy $\mu(x, y) = \mu(x, y, E)$, the first and the second measurement values are also dependent on the energy:

$$I(p,\theta,E) = \int I_0(E) \exp(-\int \mu(x,y,E)ds)dE \qquad (1)$$

A reduction of the radiation intensity by the changing of the X-ray tube voltage (anode voltage) during the second measuring cycle is accompanied by a change of the radiation energy spectrum, so that after the conversion in the device 23 the second absorption values $Q_2(p,\theta)$, having been determined along measuring paths through the examination zone 11, usually deviate from the first absorption values $Q_1(p,\theta)$ determined along the same measuring path. The deviation is at least approximately corrected by a correction factor $C(\theta)$ which is defined as follows:

$$C(\theta) = \frac{1}{K(\theta)} \sum_p Q_1(p,\theta)/Q_2(p,\theta) \qquad (2)$$

and which is dependent on the measuring direction $\theta$. Therein, $K(\theta)$ indicates the number of measuring paths through the examination zone 11 in a direction $\theta$. The sum covers all measuring paths associated with a measuring direction $\theta$ and extending through the examination zone 11.

When the intensity variation of the X-ray source 1 is realized by variation of the tube current whilst the tube voltage remains the same, the correction value will be $C(\theta) = 1$, because the radiation energy spectrum does not change, so that the first and the second measuring values are measured with the same kind of radiation. For the determination of the approximated second absorption values $Q'_2(p,\theta)$ whose associated measuring paths extend outside the examination zone 11, the second absorption values $Q_2(p,\theta)$, for measuring paths outside the examination zone 11, are multiplied by the correction factor $C(\theta)$, so that:

$$Q'_2(p,\theta) = C(\theta) \cdot Q_2(p,\theta) \qquad (3)$$

The divider/adder circuit 35 shown in FIG. 3 determines the quotient $Q_1(p,\theta)/Q_2(p,\theta)$ of the first and the second absorption value $Q_1(p,\theta)$ and $Q_2(p,\theta)$ entering via the data line 30 and measured along the same measuring path, for this measuring path and also sums the successively calculated quotients. The calculation is performed for all measuring paths extending through the examination zone 11 under the control of the position data p' entering via the third data line 32. A counter 36 determines the number $K(\theta)$ of measuring paths extending through the examination zone 11 in a measuring direction $\theta$ and applies the number $K(\theta)$ to a divider circuit 37 which determines the correction value $C(\theta)$ from the sum of the quotients and the number $K(\theta)$ (see formule 2). In a multiplier 38, the approximated second absorption values $Q'_2(p,\theta)$ for measuring paths extending outside the examination zone 11 are determined by multiplying the absorption value $Q_2(p,\theta)$ by $C(\theta)$ (see formule 3). The approximated absorption values $Q'_2(p,\theta)$ are applied to the memory 26 again via the data line 34 (FIG. 2). The second absorption values $Q_2(p,\theta)$ for measuring paths outside the examination zone 11 are thus replaced by the approximated absorption values $Q'_2(p,\theta)$. Said operations are successively performed for each measuring direction $\theta$. Subsequently, the absorption distribution $\mu(x, y)$ is determined in known manner by means of a known central computer 29 which utilizes the first absorption values $Q_1(p,\theta)$ together with the approximated second absorltion values $Q'_2(p,\theta)$.

If the absorption has to be determined within a body volume, several (for example, 20) parallel and adjoining body slices of a zone of the body can be irradiated. When use is made of a computer tomography apparatus as shown in FIG. 1 or FIG. 1a, the slices are then successively irradiated. It is not necessary to irradiate the part of the positioning zone 4 which is situated outside the examination zone 11 for each slice to be examined. In the case of examination of only a few adjoining slices, it is sufficient to irradiate only the central slice during a first as well as during a second measuring cycle. Merely the examination zone of the other slices is irradiated only during a first measuring cycle. The measuring values of the environment of the examination zone 11, derived from said central slice during the second measuring cycle, are then used for the reconstruction of an absorption image of the adjoining slices as if these measurement values had been measured in the slice to be reconstructed. If the part of the body 6 situated outside the examination zone 11 is "continuous" (i.e. if it exhibits few absorption transients from one slice to another), there will be no significant errors in the reconstructed images.

Instead of the successive irradiation of the separate slices of the body, it is alternatively possible to irradiate the various slices of the body 6 simultaneously when use is made of the detector D' shown in FIG. 6a which replaces the detector D shown in FIG. 1. To this end, the detector D' comprises several rows of detectors R, each row R detecting the radiation which passes through the examination zone 11 in a slice. The detector D' furthermore comprises one long detector row R' which detects in one slice the radiation passing through the examination zone 11 as well as radiation passing through the part of the positioning zone 4 which is situated outside the examination zone 11. During the first measuring cycle, the ends 54 are then shielded against radiation by means of a known, adjustable diaphragm which is arranged between the source 1 and the body 6. After the first measuring cycle, the diaphragm is adjusted so that all detector rows R are shielded against radiation.

If a substantial part of the body 6 is to be examined, so that a significant number of adjoining slices have to be irradiated (for example, from 10 to 20 slices), it is useful to determine measurement values in the part situated outside the examination zone in two or more slices instead of only one slice during a second cycle. These slices should then be more or less uniformly distributed among all slices. By interpolation or extrapolation between the measurement values from the second measuring cycle fictitious measurement values can thus be calculated for those slices for which no measurement values have been determined during the second measuring cycle. In addition to the successive irradiation of the adjoining slices by means of the device shown in the Figure, the detector D'' shown in FIG. 6b also enables the irradiation of different slices during a first as well as during a second measuring cycle. To this end, the detector D'' comprises two long detector rows R' for the measurement of radiation which passes through slices in the entire positioning zone 4, and detector rows R for measuring radiation which passes through the examination zone 11.

Figure 6B:
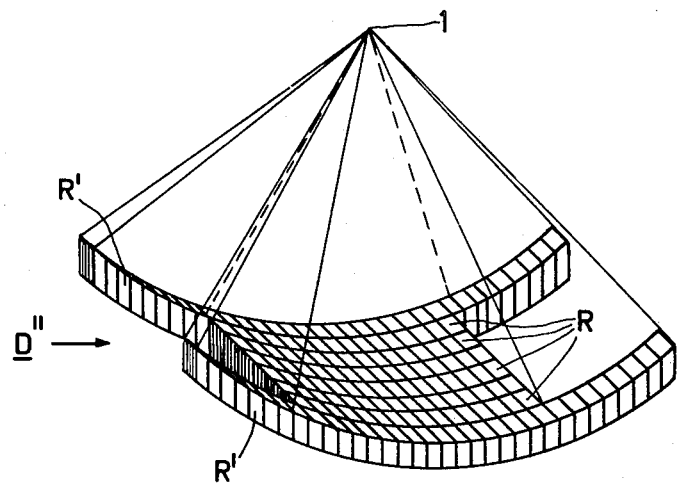

It is assumed that the detector D'' shown in FIG. 6b comprises twenty detector rows in total, only the first and the last detector row R' thereof measuring radiation which passes alongside the examination zone 11.

The second absorption values of the first and the last (for example, the twentieth) body slice determined are denoted as $Q_2^{(1)}(p,\theta)$ and $Q_2^{(20)}(p,\theta)$. The first, and the last body slice and the further body slices situated therebetween are irradiated during a first measuring cycle in order to obtain the first absorption values $Q_1^{(n)}(p,\theta)$ ($1 \leq n \leq 20$). The letter n denotes the number of a body slice.

It is assumed hereinafter that the position and the size of the examination zones in the adjacent body slices are the same in each body slice. If the position and the size of the examination zones deviate, the various formules have to be changed accordingly. However, this does not affect the basic idea of the invention.

Using the method of determining the absorption distribution $\mu(x, y)$ within a body slice as described with reference to FIG. 3, the approximated second absorption values $Q'_2{}^{(n)}(p,\theta)$ are determined only for the first and the twentieth body slice. Absorption values to be determined along measuring paths which are situated outside an examination zone in an $n^{th}$ body slice between the first and the twentieth body slice are determined by means of the second absorption values $Q_2^{(1)}(p,\theta)$ or by means of the second absorption values $Q_2^{(20)}(p,\theta)$ or by interpolation between these two absorption values.

An embodiment for determining the approximated second absorption values $Q'_2{}^{(n)}(p,\theta)$ for an $n^{th}$ body slice is described by the following equations 4 and 5:

$$Q'_2{}^{(n)}(p,\theta) = C(\theta)^{(n)} \cdot Q_2^{(1)}(p,\theta) \text{ for } n=2, 3, \ldots 19 \quad (4)$$

where $$C(\theta)^{(n)} = \frac{1}{K(\theta)} \sum_p Q_1^{(n)}(p,\theta)/Q_2^{(1)}(p,\theta) \quad (5)$$

The quotient $Q_1^{(n)}(p,\theta)/Q_2^{(1)}(p,\theta)$ is formed from the first absorption values $Q_1^{(n)}(p,\theta)$ of the relevant body layer n and from the second absorption values $Q_2^{(1)}(p,\theta)$ of the first body slice along measuring paths extending through the examination zone in the body slice n in the measuring direction $\theta$. The sum of all quotients associated with the measuring direction $\theta$ is divided by the number $K(\theta)$ which indicates the number of measuring paths extending through the examination zone of the relevant body slice for a measuring direction.

The second absorption values $Q_2(p,\theta)$ of the first body layer are multiplied (see formule 4) by the correction factor $C(\theta)^{(n)}$ for each direction $\theta$ in order to determine approximated second absorption values $Q'_2{}^{(n)}(p,\theta)$ for the $n^{th}$ body slice associated with the measuring paths extending outside the examination zone.

This method, where each time the first absorption value $Q_2^{(1)}(p,\theta)$ of the first body slice is used in order to obtain the absorption distribution of an $n^{th}$ body slice, however, produces only an approximate absorption distribution in the successive $n^{th}$ body slices. The results may be displayed, for example, as a provisional analysis on the monitor 30 (FIG. 2).

However, when all measurement values are available, so that the first and the last (the twentieth) body slice have been irradiated during a first and a second measuring cycle, whilst the intermediate body slices have been irradiated only during a first measuring cycle for the determination of first absorption values $Q_1^{(n)}(p,\theta)$, the second absorption values $Q_2^{(20)}(p,\theta)$ can be used for determining second absorption values in the intermediate body slices. An approximated second absorption value $Q'^{(n)}(p,\theta)$ for a measuring path in an $n^{th}$ body slice is then determined, for example, by:

$$Q'_2{}^{(n)}(p,\theta) = \overline{C(\theta)}^{(n)}\{Q_2^{(1)}(p,\theta)\cdot a^{(n)} + Q_2^{(20)}(p,\theta)\cdot b^{(n)}\} \quad (6)$$

in which $a^{(n)}$ and $b^{(n)}$ are interpolation factors which are, for example, equal to:

$$a^{(n)} = \frac{20 - n}{20} \quad (7)$$

and $$b^{(n)} = 1 - a^{(n)}, \quad (8)$$

and wherein:

$$\overline{C(\theta)}^{(n)} = \frac{1}{K(\theta)} \sum_p Q_1^{(n)}(p,\theta)/\{Q_2^{(1)}(p,\theta)a^{(n)} + Q_2^{(20)}(p,\theta)b^{(n)}\} \quad (9)$$

The correction factor $\overline{C(\theta)}^{(n)}$ depends on the second absorption values in the first and the twentieth body slice. Thus, for an $(n)^{th}$ body slice approximated second absorption values $Q'_2{}^{(n)}(p,\theta)$ are obtained for measuring paths outside the examination zone in the $n^{th}$ slice.

FIG. 4 shows a block diagram of a circuit 28' for executing the described methods. The circuit 28' comprises a memory 39 in which all first absorption values $Q_1^{(1)}(p,\theta), \ldots, Q_1^{(n)}(p,\theta), \ldots, Q_1^{(20)}(p,\theta)$ and the second absorption values $Q_2^{(1)}(p,\theta), Q_2^{(20)}(p,\theta)$ measured in the first and the twentieth body slice are stored.

The interpolation factors $a^{(n)}$ and $b^{(n)}$ are stored in a memory 40. After completion of all measuring cycles for the irradiation of the 20 body slices, the multiplier and adder circuit 41 successively performs two multiplications for each p for each measuring direction and for each slice (see formula 6): $Q_2^{(1)}(p,\theta)a^{(n)}$ and $Q_2^{(20)}(p,\theta)b^{(n)}$. For each body slice 2, 3, ... 19, the sum of both multiplications is stored in the memory 39, whilst the number $K(\theta)$ counted by the counter 36 is stored in a memory 42 for each measuring direction $\theta$ and each layer n after the calculations for a measuring direction. The elements denoted by the reference numerals 35, 36, 37, 38 correspond to the elements in FIG. 3 which are denoted by the same reference numerals. The first absorption values $Q_1^{(n)}(p,\theta)$ stored in the memory 39 are returned, together with the approximated second absorption values $Q'_2{}^{(n)}(p,\theta)$, via the data lines 43 and 34, to the second memory 26 (see FIG. 2), so that they are available for determining the absorption distribution in the various body slices.

For the determination of the absorption distribution in a three-dimensional part of the body 1 it is also possible to irradiate the entire positioning zone of the first and the twentieth body slice in only one measuring cycle with the first intensity $I_{01}$ in order to determine first absorption values $\overline{Q_1}^{(1)}(p,\theta)$ for the first body slice and $\overline{Q_1}^{(20)}(p,\theta)$ for the twentieth body slice, respectively. The approximated second absorption values $Q'_2{}^{(n)}(p,\theta)$ for an intermediate body slice n are then determined as follows:

$$Q'_2{}^{(n)}(p,\theta) = \overline{Q}_1^{(1)}(p,\theta)\cdot a^{(n)} + \overline{Q}_1^{(20)}(p,\theta)b^{(n)} \quad (10)$$

in which $a^{(n)}$ and $b^{(n)}$ are determined by the formulas (7) and (8). The measuring paths associated with the various absorption values occupy approximately the same position with respect to the system axis 2 in said body slices. The absorption distribution $\mu(x, y)$ of the body slice (n) is reconstructed by means of the approximated absorption values $Q'_2{}^{(n)}(p,\theta)$ and the first absorption values $Q_1^{(n)}(p,\theta)$ whose associated measuring paths extend through the examination zone of the intermediate body slice n. Because only one measuring cycle is performed for the first and the twentieth body slice, the overall measuring time is thus further reduced.

It will be clear that particularly the detectors shown in the FIGS. 6a and b can be used for the described method. The overall measuring time required for all n different slices is then reduced to the measuring time required for a single slice. This is notably important because the body 6 must be in rest during the measurement. Artefacts in the images to be reconstructed are prevented by the reduction of the measuring time because, for example, holding the breath is very well feasible for 4 to 6 seconds (measuring time for a slice), but a measuring time of from 40 to 60 seconds (ten slices) would already give rise to problems.

The reconstruction methods customarily used thus far do not take into account the fact that the correction of the second absorption values $Q_2^{(n)}(p,\theta)$ by multiplication by the correction factor $C(\theta)$, $\overline{C}^{(n)}(\theta)$ forms only an approximation of the first absorption values $Q_1^{(n)}(p,\theta)$. Local deviations cannot be eliminated thereby. Local deviations of this kind, however, occur, for example, between first absorption values $Q_1(p',\theta)$ and approximated second absorption values $Q'_2(p',\theta)$, where p' is the position or the path of an extreme ray which is tangent to the examination zone 11. Due to the stepwise transients between $Q_1(p',\theta)$ and $Q'_2(p',\theta)$ local artefacts may occur in the reconstructed absorption distribution.

In order to avoid this, a local adaptation of the approximated second absorption values $Q'_2(p',\theta)$ to the first absorption values $Q_1(p',\theta)$ is realized for each examination zone and for each measuring direction $\theta$ by a more elaborate correction.

The more elaborate correction is executed in accordance with the formula $$Q''_2{}^{(n)}(p,\theta) = d^{(n)}(p,\theta)\cdot Q'_2{}^{(n)}(p,\theta); \text{ where } n = 1, 2, \ldots 20 \quad (11)$$

Therein, the absorption values $Q'_2{}^{(n)}(p,\theta)$ are the approximated second absorption values already calculated by the arithmetic unit 38 (see FIG. 3). The absorption value $Q''_2{}^{(n)}(p,\theta)$ is the corrected approximated second absorption value associated with a measuring path outside an examination zone 11. The factor $d^{(n)}(p,\theta)$ is a second correction factor which realizes a monotonously decreasing transition from the first absorption values $Q_1^{(n)}(p,\theta)$ in position $p < p'$ to the approximated second absorption value $Q'_2{}^{(n)}(p,\theta)$ in the position $p > p'$, the second correction factor satisfying, for example:

$$d^{(n)}(p,\theta) = 1 - f(p - p') + \frac{Q_1^{(n)}(p',\theta)}{Q'_2^{(n)}(p',\theta)} \cdot f(p - p') \quad (12)$$

Therein, f(p-p') is a weighting function which monotously decreases as a function of the distance, where f(p-p')=1 for p-p'=0 and f(p-p')<1 for |p-p'|0. The limitation of the more elaborate correction to a local range of the absorption values is obtained by a suitable choice of a weighting factor f(p-p').

The elements denoted by the reference numerals 35 to 42 in FIG. 4 correspond to the elements bearing these reference numerals in FIG. 5. As appears from FIG. 5, the approximated second absorption values $Q'_2^{(n)}(p,\theta)$ obtained by means of the multiplier 38 are applied, via a data line 48, to the memory 39 in order to replace the absorption sums $Q_2^{(1)}(p,\theta)a^{(n)} + Q_2^{(20)}(p,\theta)b^{(n)}$ stored therein. In the divider 44 the quotients $Q_1^{(n)}(p',\theta)/Q'_2^{(n)}(p',\theta)$ (see formule 12) are formed and from a memory (for example, a read-only memory) the weighting factors f(p-p') are retrieved, after which the second correction factor $d^{(n)}(p,\theta)$ is determined by means of the multiplier/adder 46. The second correction (see formule 11) is subsequently performed in the multiplier 47 whereto, therefore, the second correction factor $d^{(n)}(p,\theta)$ and the second approximated absorption value $Q_2^{(n)}(p,\theta)$ are applied from the memory 39.

The method illustrated by the block diagram of FIG. 5 is also suitable for adequate correction of deviations between first absorption values $Q_1^{(n)}(p,\theta)$ and second absorption values $Q_2^{(n)}(p,\theta)$ caused by patient movements. The more elaborate corrected approximated second absorption value $Q''_2^{(n)}(p,\theta)$ is introduced into the memory 26 via data line 34.

The method in accordance with the invention is not restricted to use in computer tomography apparatus comprising a detector device which moves with the source as shown in FIG. 1, but can also be used in computer tomography apparatus comprising a single detector or some tens of detectors or a stationary detector device which comprises a closed ring of detectors.

What is claimed is:

1. A method for determining the distribution of radiation absoption properties in a body by computed tomography which includes the steps of:
   radiating a planar examination zone in the body, from a plurality of directions, with radiation having a first intensity so that the radiation passes through the examination zone along a large number of measurement paths in the plane of the examination zone, collimating said radiation so that the radiation having a first intensity does not pass through the body along paths which do not pass through the examination zone, and measuring the intensity of the radiation which has passed through the examination zone along the paths to obtain as a first set of measurement values;
   radiating a positioning zone, which lies in the plane of and completely encloses the examination zone, from a plurality of directions with radiation having a second intensity which is smaller than the first intensity, so that the radiation passes through the positioning zone along a large number of measurement paths in the plane of the zones, and measuring the intensity of the radiation which has passed through the positioning zone to obtain a second set of measurement values;
   calculating first absorption values from the first set of measurement values;
   calculating second absorption values from the second set of measurement values; and
   reconstructing the distribution of radiation absorption properties in the examination zone from using the first absorption values and the second absorption values.

2. A method for determining the distribution of radiation absorption properties in a body by computed tomography comprising the steps of:
   utilizing the method of claim 1 to reconstruct the distribution of radiation absorption properties in a first planar slice of the body;
   displacing the body in a direction transverse to the slice plane to radiate further body slices which are situated parallel to and adjacent to the first body slice;
   radiating further parallel, planar examination zones in one or more of the further slices of the body, from a plurality of directions with radiation having the first intensity so that the radiation passes through the further examination zones along a number of measurement paths; measuring the intensity of the radiation which has passed through the further examination zones along the measuring paths to obtain further first sets of measurement values;
   calculating further first sets of absorption values from the further first sets of measurement values;
   approximating a second set of absorption values for the further slices from the second set of measuring values which were obtained while radiating the first slice along measuring paths which extend outside of the examination zone; and
   utilizing the further first sets of absorption values and the further second sets of absorption values to reconstruct radiation absorption distributions in the further slices.

3. A method as claimed in claim 1 or 2 further comprising the steps of producing the radiation with a X-ray tube and changing the intensity of the radiation between the first intensity and the second intensity by changing a current in the X-ray tube.

4. The method of claim 1 or 2 further comprising the steps of producing the radiation with an X-ray tube and changing the intensity of the radiation between the first intensity and the second intensity by changing a voltage applied to the X-ray tube.

5. A method as claimed in claim 1 or 2 further comprising the step of producing the radiation from a radiation source, wherein the step of radiating the examination zone with radiation of a first intensity comprises situating the radiation source at a first distance from the examination zone and wherein the step of radiating the positioning zone with radiation of the second intensity comprises situating the radiation source at a second distance, which is larger than the first distance, from the examination zone.

6. Computed tomography apparatus for determining the distribution of radiation absorption properties in a planar slice of a body comprising:
   radiation source means which generate a planar beam of penetrating radiation and radiate a plane in the body therewith from a plurality of directions;
   detector means which measure radiation from the radiation source means which has passed through the body and which determine therefrom absorption values which are a measure of the radiation attenuation along measuring paths in the plane which pass through the body from the source;

a positioning zone for the body situated between the source means and the detector means;

central processing means which determine absorption coefficients of the radiation absorption distribution from the absorption values;

a memory for storing the absorption values and the absorption coefficients; and display means which display the radiation absorption distribution;

wherein an examination zone in the plane lies within and is wholly surrounded by the positioning zone and, as an improvement, the apparatus further comprises:

means which operate the radiation source means to produce two different intensities of radiation so that a first, higher intensity of radiation is used to radiate the body along paths which pass through the examination zone and a second, lower intensity of radiation is used to radiate the body along all paths which pass through the entire positioning zone, the higher intensity radiation being used to determine a first set of absorption values and the lower intensity of radiation being used to determine a second set of absorption values; and arithmetic means which determine the number k of measuring paths which extend through the examination zone in each direction, which determine and sum quotients of the first absorption values $Q_1(P_1, \theta)$ and second absorption values $Q_2(P_2, \theta)$ associated with the measuring paths, which divide the sum thus obtained by the number of measuring paths, thereby determining a correction factor $C(\theta)$ in accordance with the formula $$C(\theta) = ((\upsilon(Q_1(P_1,\theta)/Q_2(P_1,\theta))k$$

and which multiply those second absorption values which were measured along measuring paths in that direction which pass through the positioning zone and do not pass through the examination zone by the correction factor.

7. A device as claimed in claim 6 wherein the detector means comprises:

two long, parallel rows of detector elements disposed opposite the radiation source means to receive radiation which has passed through the positioning zone, the detector elements at the ends of the long rows being disposed to receive radiation from the source means along paths which are tangent to the perimeter of the positioning zone;

one or more short rows of detectors disposed between the long rows and parallel thereto to receive radiation from the source which has passed through the examination zone, and wherein the apparatus further comprises interpolation means which calculate interpolated values from the absorption values supplied by the long detector rows.

* * * * *

UNITED STATES PATENT AND TRADEMARK OFFICE
CERTIFICATE OF CORRECTION

PATENT NO. : 4,394,738
DATED : July 19, 1983
INVENTOR(S) : WOLFGANG WAGNER

It is certified that error appears in the above-identified patent and that said Letters Patent are hereby corrected as shown below:

Claim 6, Column 16, Line 5 change
"$C(\theta)=((\ v(Q_1(P_1,\theta)/Q_2(P_1,\theta)k$" to
--$C(\theta)=((\sum(Q_1(P_1,\theta)/Q_2(P_1,\theta)k$-- .

Signed and Sealed this

Twentieth Day of September 1983

[SEAL]

Attest:

GERALD J. MOSSINGHOFF

Attesting Officer     Commissioner of Patents and Trademarks